United States Patent [19]

Lasker et al.

[11] Patent Number: 5,595,987

[45] Date of Patent: Jan. 21, 1997

[54] METHOD OF SLOWING VENTRICULAR ARRHYTHMIAS USING ZATEBRADINE

[75] Inventors: Steven Lasker, New York; Richard Klein, Bronx, both of N.Y.

[73] Assignee: The Trustees of Columbia University in the City of New York, New York, N.Y.

[21] Appl. No.: 231,480

[22] Filed: Jul. 22, 1994

[51] Int. Cl.$^6$ .................................................. A61K 31/55
[52] U.S. Cl. ............................................ 514/213; 514/821
[58] Field of Search ..................................... 514/213, 821

[56] References Cited

U.S. PATENT DOCUMENTS 4,490,369   12/1984   Reiffen et al. ........................ 424/244

OTHER PUBLICATIONS

CA 120:182730q, Goethals et al., 1993.
CA 120:235793w, Bril et al., May 9, 1994.

*Primary Examiner*—Kimberly Jordan
*Attorney, Agent, or Firm*—John P. White

[57] ABSTRACT

The present invention relates to a method of using zatebradine by intravenous (IV) injection to retard or eliminate arrhythmias due to abnormal spontaneous activity in subendocardial Purkinje fibers. More specifically, the present invention relates to the use of zatebradine to reduce intracellular $Na^+$ activity in Purkinje fibers and block $I_f$ current. Arrhythmias due to abnormal spontaneous activity in subendocardial Purkinje fibers occur 24 hours after occlusion of the left anterior descending (LAD) coronary artery in canine heart. These Purkinje fibers in the infarcted hearts are depolarized and have elevated intracellular $Na^+$ activity. The major current underlying normal automaticity in these fibers is the $I_f$ current. Zatebradine reduces intracellular $Na^+$ activity in Purkinje fibers by 4 mM. In vivo, 0.25–1.0 mg/kg intravenous injections of zatebradine slow ventricular rhythms by 24%. Although zatebradine also slows sinus nodal rate, it precipitates a more severe arrhythmia. However, during right atrial pacing, capture of ventricular rhythms occurs at lower rates (i.e. 28% reduction) in the presence of zatebradine. Thus, zatebradine eliminates the arrhythmia when the right atria is paced at the original sinus rate.

7 Claims, 4 Drawing Sheets

1 sec

METHOD OF SLOWING VENTRICULAR ARRHYTHMIAS USING ZATEBRADINE

FIELD OF INVENTION

The present invention relates to the use of zatebradine to retard or reduce ventricular rhythm due to abnormal spontaneous activity in subendocardial Purkinje fibers. More specifically, the present invention relates to the use of zatebradine to retard or reduce ventricular rhythm by blocking $I_f$ current in Purkinje fibers, and in addition, zatebradine lowers intracellular $Na^+$ activity, which may be therapeutic in itself, possibly by retarding arrhythmias.

BACKGROUND OF THE INVENTION

Arrhythmias are caused by abnormalities in the cell membrane where electrical signalling is generated. Alterations in normal signal generation or propagation lead to disordered cardiac electrical activity, that is, arrhythmias, which can severally and lethally compromise the cardiac function of pumping oxygenated blood. Arrhythmias following myocardial infarction have become a significant public health problem. For example, following occlusion of a coronary artery, arrhythmias develop due to the ensuing ischemia and infarction. Further, following an acute period of approximately one hour, there is a second risk period which generally occurs between 18 and 72 hours, referred to as the delayed phase, during which arrhythmias, predominantly ventricular tachycardia, (i.e. rapid rhythms) occur.

The primary research approach to studying arrhythmias is by use of animal models, of which the canine is the most important. The major animal model for studying these arrhythmias is the Harris 24 hour dog infarct model, typically generated by a two stage ligation of the left anterior descending (LAD) coronary artery. A surgical ligature around this major artery, which normally provides blood for a portion of the left ventricle, acts to induce a myocardial infarction, thus simulating a "heart attack". This model is studied at 24 hours after the coronary artery ligation, at which time ventricular arrhythmias are generally seen. The locus of origin of these arrhythmias in the experimental model is the subendocardial Purkinje cell layer over the infarct (generally the apical region of the left ventricle). These Purkinje cells survive, but have depolarized membrane potentials and rapid abnormal spontaneous activity. The rapid abnormal spontaneous activity generated in these abnormal cells subsequently spreads throughout the ventricle, and, as a result, interferes with normal conduction patterns and potentially reduces cardiac output.

Elevations of intracellular sodium activity long have been known to cause so called "triggered" arrhythmias through a slightly different cellular process than the abnormal spontaneous activity referred to above (e.g. "abnormal automaticity"). We had previously measured the intracellular sodium ion activity in Purkinje fibers from 24 hour infarcts and discovered that it was elevated by more than 50%. It is believed that this increase may contribute an additional mechanism for the arrhythmias seen in this experimental model.

Antiarrhythmic therapies in the past have concentrated on drugs which block various ion channels, such as calcium channel blockers, or in some cases hormonal membrane receptors, such as beta blockers. Antiarrhythmic drugs generally are designed to bind to receptors in the cardiac membrane, some of which are themselves ion channel proteins, and in binding to normalize or otherwise ameliorate the disordered electrical activity. There are inherent disadvantages associated with these therapies. A particular severe drawback is that sufficiently high doses of these antiarrhythmic drugs needed to suppress the arrhythmias can result in deleterious side effects, including causing other, possibly more severe, arrhythmias. For example, the class I sodium channel blocker type anti-arrhythmic drugs can potential reentrant arrhythmias and central nervous system pathology, while the class II calcium channel blocker type anti-arrhythmic or beta blocker type drugs can reduce cardiac output causing additional cardiac or systemic ischemia.

An additional therapy involves the use of zatebradine. Zatebradine is a benzepine derivative, as disclosed in U.S. Pat. No 4,490,369 to Reiffen et al. Reiffen et al. found that these derivatives exhibit useful pharmocodyanmic properties, including mild hypotensive activity and selective bradycardiac activity. Vos et al. proposed the use of zatebradine in a different animal model of 24 hour arrhythmias, specifically, the Harris dog with surgical AV block (Vos, M A, Leunissen, J D, van der Zande, J, Wellens, H J (1994) "UL-FS 49, a rather selective blocker of the pacemaker current $I_f$ has no effect on automatic ventricular arrhythmias occurring 24 hours after infarction," *Journal of American College of Cardiology*, 23:183a). However, Vos et al. did not appreciate that normal sinoatrial conduction was required for zatebradine to slow arrhythmias. Surgical AV block prevents normal or paced sinoatrial conduction. Additionally, the use of zatebradine for the treatment of high blood pressure and cardiac insufficiency is taught in European patent application EP-A 88-11-7181.

A need still exists for an anti-arrhythmic therapy which slows ventricular rhythms without producing deleterious side effects. It is believed that the use of the drug zatebradine, coupled with careful atrial pacing, not only slows ventricular rhythms, but does not result in the side effects experienced with prior art therapies.

SUMMARY OF THE INVENTION

Accordingly, it is an object of the present invention to provide a method of slowing ventricular arrhythmias.

It is another object of the present invention to provide a method of slowing ectopic ventricular rhythms by an average rate of reduction of 28%.

It is another object of the present invention to provide a method of reducing $I_f$ current by introduction of the drug zatebradine.

It is an additional object of the present invention to provide a method of maintaining sinoatrial rates after introduction of the drug zatebradine by atrial pacing in order to obtain a normal pattern of atrial to ventricular conduction at a significantly lower rate.

It is still another object of the present invention to provide a rate reduction of about 28% using the canine 24 hour infarct model with atrial pacing.

It is a further object of the present invention to provide a method of slowing both the ventricular rhythm and sinus rhythm in order to convert to sinus rhythm.

Additional objects, advantages and novel features of the invention will be set forth in part in the description which follows, and in part will become apparent to those skilled in the art upon examination of the following specification or may be learned by practice of this invention.

These and other objects of the invention, as embodied and broadly described herein, are achieved by providing a method of using zatebradine by intravenous (IV) injection to retard or eliminate arrhythmias due to abnormal spontaneous activity in subendocardial Purkinje fibers. More specifically, the present invention relates to the use of zatebradine to reduce intracellular $Na^+$ activity by blocking $I_f$ current in Purkinje fibers.

DESCRIPTION OF THE DRAWINGS

The present invention will be better understood with reference to the appended drawing sheets, wherein.

DETAILED DESCRIPTION

Figure 1A:
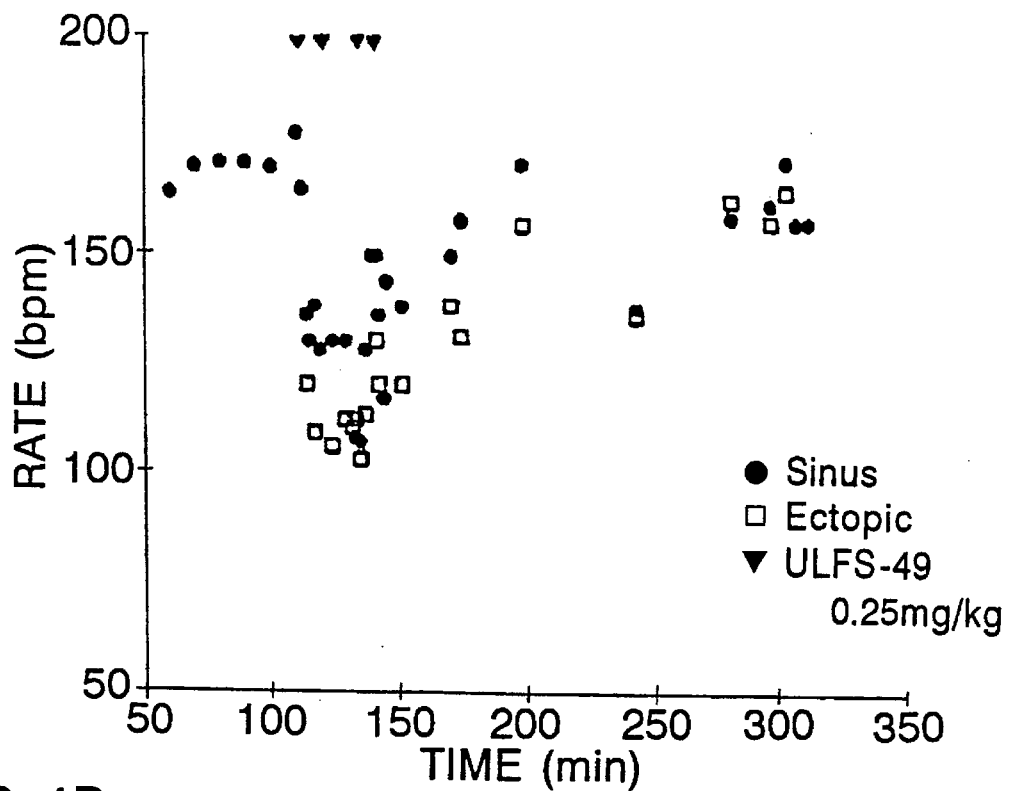
FIG. 1A depicts sinus rate (filled circles) and ectopic rate (squares) plotted versus time (horizontal axis).

The present invention relates to a method of slowing ventricular arrhythmias using the drug zatebradine. The intravenous use of zatebradine results as a therapeutic agent for slowing ventricular tachycardiac occurring in the delayed, in-hospital phase, following myocardial infarction. We hypothesize that a relatively recently discovered ion current, the so called "pacemaker" current ($I_f$) may be a significant cellular mechanism of arrhythmias. We believe that zatebradine acts directly to block this significant inward diastolic current which contributes to so called "abnormal automaticity" or "enhanced normal automaticity", both acknowledged mechanisms of the 24 hours tachyarrhythmias. $I_f$ current also is well known to contribute to inward sodium ion movement. Thus, blocking $I_f$ current results in lower intracellular sodium activity, which is anti-arrhythmic. We confirmed that intracellular sodium is lowered in Purkinje fibers removed from 24 hour infarct canine hearts and measured with sodium sensitive microelectrodes in an experimental tissue bath. Further, the zatebradine therapy of the present invention is free of various serious complications and side effects associated with the prior art of sodium and calcium channel blocker anti-arrhythmics.

In an animal model, specifically the canine model, arrhythmias due to abnormal spontaneous activity in subendocardial Purjinke fibers occur after 24 hours of the left anterior descending (LAD) coronary artery. These Purkinje fibers in the infarcted hearts are depolarized and have elevated intracellular $Na^+$ activity. The major current underlying normal automaticity in these fibers is the $I_f$ current. Although diastolic membrane potential is generally positive to the $I_f$ activation range in these depolarized fibers in infarcts, this activation range has been shown to shift in a positive direction in response to hormonal influences. Thus, $I_f$ current could still mediate automaticity in these fibers in infarcts. Since $I_f$ current activation also mediates $Na^+$ influx, the effects of an $I_f$ current channel blocker on intracellular $Na^+$ activity in vitro and on ventricular tachycardias in situ has been studied, using 24 hour canine infarcts. We discovered that 0.25–1.0 mg/kg intravenous injections of zatebradine reduces intracellular $Na^+$ activity in Purkinje fibers by 4 mM, resulting in a slowing of ventricular rhythms by 24%. However, zatebradine also slows sinus nodal rate, thereby precipitating a more severe arrhythmia. In order to overcome the slowing of the sinus nodal rate, right atrial pacing was performed, resulting in capture of ventricular rhythms at lower rates, significantly, as much as a 28% reduction, in the presence of zatebradine. Accordingly, zatebradine eliminates the arrhythmia when the right atria is paced at the original sinus rate.

The use of zatebradine blocks inward diastolic currents in Purkinje fibers. These diastolic currents contribute to spontaneous activity in the depolarized subendocardial Purkinje fibers surviving in 24 hour canine infarcts. The most likely current affected is the $I_f$ current. Although it is unclear as to whether zatebradine acts on the most depolarized and rapidly automatic fibers, its performance is sufficient to slow fibers coupled to them to reduce the rate of the ectopic focus.

Over the infarct, the Purkinje fiber membrane potential is depolarized. This depolarized membrane potential was generally thought to be more positive than the normal activation range ("operating range") of the $I_f$ current. However, hormonal modulation which elevates cyclic AMP can shift the activation range in the positive direction so that this current would then be operative even for a range of depolarized membrane potentials. Our recent experiments also have shown that Zatebradine lowers intracellular sodium ion activity, which itself is antiarrhythmic in that it lowers the probability of "triggered" automatic activity.

EXAMPLE I

Preparation of Canine Infarct

Adult mongrel dogs, conditioned for survival surgery and weighing 20–30 kilograms, were anesthetized using 1.5–2.0% isoflurane with oxygen, followed by endotracheal intubation. The dogs were immediately ventilated mechanically with a Harvard Respiration Pump (Harvard Apparatus Co., Inc., Dover, Mass.). The Left Anterior Descending artery (LAD) was ligated in a two-stage process via a left thoracotomy as described by Harris et al. The dog was allowed to recover over the ensuing 24 hours, after which it was reanesthetized with 15 mg/kg sodium pentobarbital. The dog was then intubated and mechanically ventilated. Maintenance of anesthesia consisted of intermittent boluses of sodium pentobarbital. A midline sternotomy was performed. The chest was covered with a plastic drape and a heat lamp was lit over the dog's chest to maintain an internal temperature of 35.5° to 36.0° C. An intravenous line was used for all peripheral injections, and a standard five lead ECG was placed via needle electrodes. All animal procedures were approved by the Columbia Animal Care and Use Committee of the Department of Comparative Medicine.

EXAMPLE 2

Experimental Design for Whole Animal Studies

All dogs were prepared as described above. Baseline electrocardiographic tracings of leads II and V5 were recorded on a Gould chart recorder for control periods of 30–60 minutes, followed by either intravenous or intracoronary injections. The injections consisted of bolus intravenous injections of zatcbradine in doses ranging rom 0.25–1.0 mg/kg. Recordings of the ECG were analyzed for both rate and rhythm (sinus versus ectopic). Rate was measured at frequent, regular intervals (5–10 min) and was calculated by dividing the number of beats by the interval duration. Sampling was more frequent just before and after drug interventions. Two displays were used. One display shows rates for both sinus and ventricular rhythms (separate symbols, vertical axis). The other display shows the percentage of beats that were of sinus or ventricular origin. The horizontal axis indicates experimental time where zero represents the first ECG recording taken from an anesthetized closed chested animal.

To determine the effect of zatebradine on the ventricular ectopic rhythms while avoiding influences due to the changing sinoatrial rate, right atrial pacing was employed. Pacing was accomplished with a wire lead ligated to the right atrium and delivering 2 msec pulses at twice threshold. The criteria for judging efficacy of pacing was determined by the percent captured beats during a one minute interval. An initial warmup period, generally less than 15 seconds, was allowed before starting the one minute test interval during which capture was quantitated.

EXAMPLE 3

Control occurrence of arrhythmias

ECG measurements were performed in eight (8) dogs surviving two stage LAD ligation for 24 hours. A variety of presentations in terms of the severity of arrhythmias, and the rate and prevalence of ventricular versus sinus rhythms, was observed. A total of three (3) dogs had almost pure sinus rhythm with only incidental ventricular beats. Most dogs (n=5) had significant ventricular rhythms (e.g. 36% to 100% of total beats during the control period).

EXAMPLE 4

Intravenous Intervention with Zatebradine

Six (6) dogs were administered intravenous boluses of zatebradine. In 3 of these dogs, a dose of 0.25 mg/kg was injected, and in the other 3 a dose of 1.0 mg/kg was injected. Minimum ventricular rate following drug injection was compared to ventricular rate just prior to injection (slowest rates usually occurred within several minutes after the injection). Since the two doses showed comparable effects, we pooled the n=6 experiments. In instances when there was pure sinus rhythm during control (n=2), we used the last ventricular rhythms measured during drug washout for the control rate. This was determined to be a reasonable procedure from experiments where there were ventricular beats during control. Zatebradine significantly reduced ventricular rate from 152.3±22.1 beats/min to 117.0±20.3 beats/min (SEM; $p<0.001$). Table 1 sets forth the values of individual experiments:

TABLE I

Effects of Zatebradine on Rate of Ventricular Rhythms

| Trial # | Control Rate (beats/min) | Rate after Zatebradine (beats/min) | Intravenous dose (mg/kg) |
| --- | --- | --- | --- |
| 1 | 185 | 152 | 0.25 |
| 2 | 165 | 103 | 0.25 |
| 3 | 120 | 97 | 0.25 |
| 4 | 150 | 112 | 1.0 |
| 5 | 140 | 109 | 1.0 |
| 6 | 154 | 129 | 1.0 |

Figure 1B:
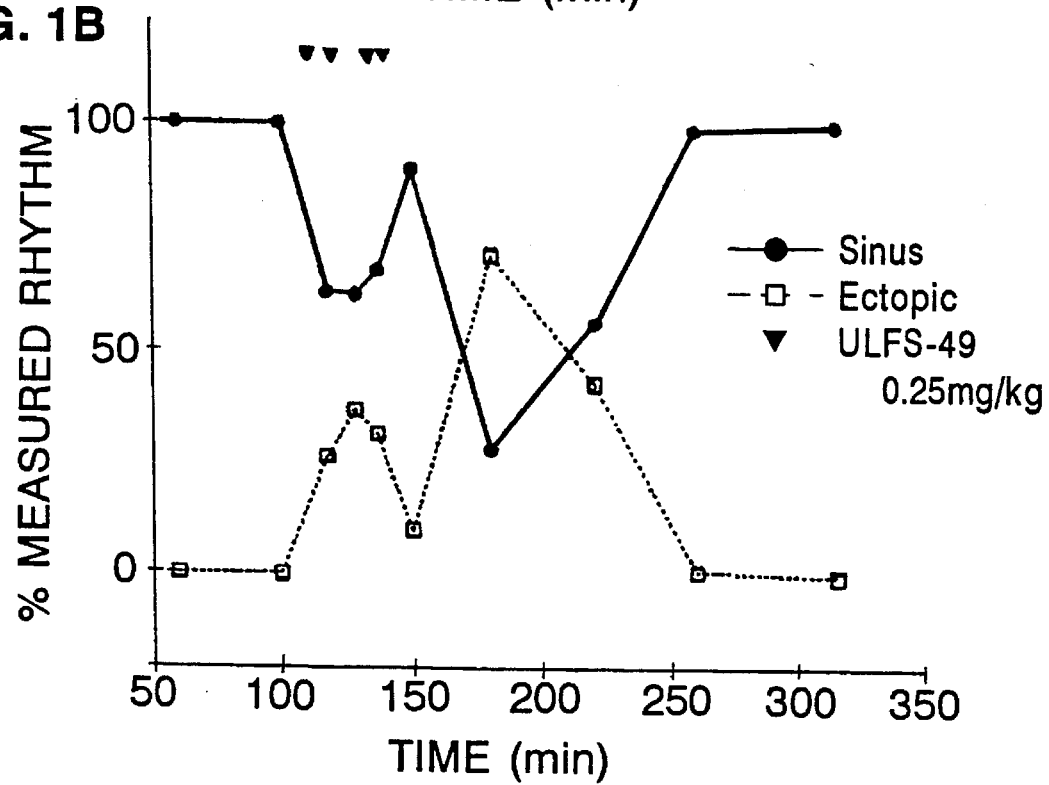
FIG. 1B depicts sinus rhythm (filled circles) and ectopic rhythm (squares) plotted versus time (horizontal axis).
Figure 2A:
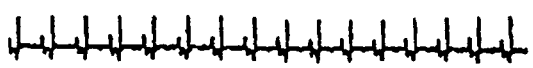
FIG. 2 depicts a series of six ECG traces data plotted from FIG. 1.
Figure 2B:
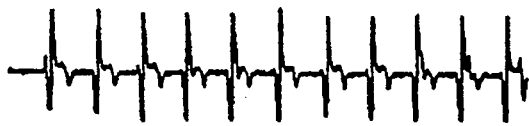
Figure 2C:
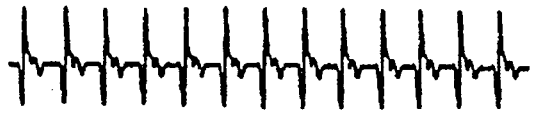
Figure 2D:
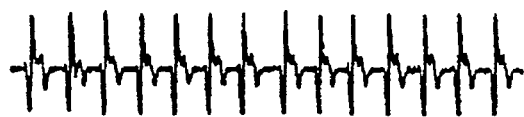
Figure 2E:
Figure 2F:
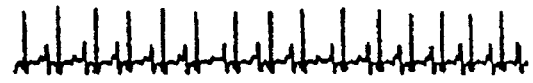
Figure 3A:
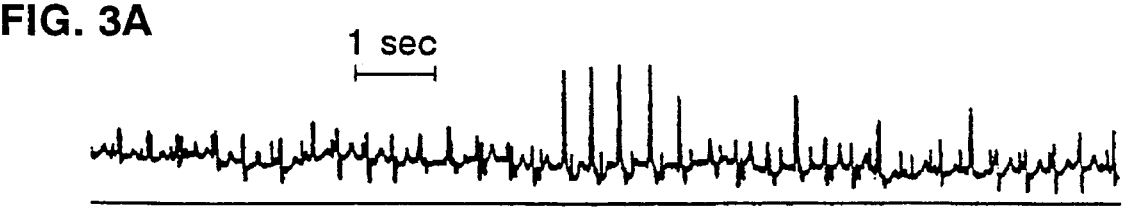
FIG. 3 depicts configurations during trains of stimuli applied to the right atria 24 hrs after ligation.
Figure 3B:
Figure 3C:
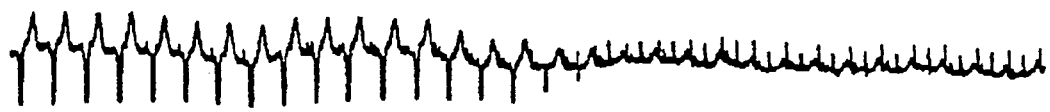
Figure 3D:
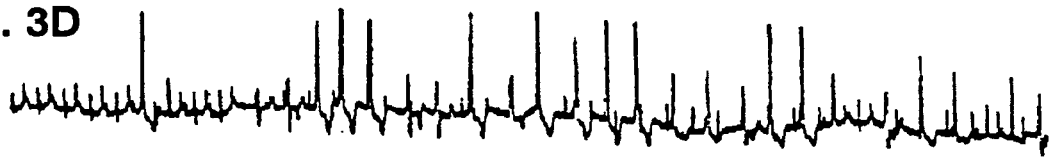

The results of these findings are depicted in FIGS. 1A and 1B. Sinus and ventricular rates versus time are illustrated in FIG. 1A. There was pure sinus rhythm (darkened circles) prior to drug injection. Fifty minutes of stable sinus baseline activity are plotted prior to the first drug injection. Four bolus injections of 0.25 mg/kg zatebradine (UL-FS 49) each then were administered, as shown by the darkened arrows. Following the initial injections, the sinus rate was reduced from the initial value of 170/min to a low of 110/min. The sinus rate recovered toward the initial value of 170/min for two hours following the last injection. Ectopic ventricular rhythms (squares) are also seen and recovered (speed up) over a similar time course. Initial (pre-drug) ectopic rates are not known since the pre-drug rhythm was pure sinus.

The percent of ventricular versus sinus beats for this same trail #1 is plotted in FIG. 1B. Beginning just after the first intravenous injection, the percent sinus rhythm fell from 100% to 29% while the percent ventricular rhythm rose from 0% to 71%. By two hours after the last injection, the rhythm had returned to pure sinus. The percentage of beats in sinus rhythm (darkened circles) versus ectopic rhythm (squares) is also plotted against the same time axis. They rhythm is initially pure sinus (i.e., 100%); the percent sinus then falls to below 30% at 40 minutes after the last injection. They rhythm then returns to being predominantly and then completely sinus. The experimental preparation was started at time zero.

Following the first injection, sinus rates fell from approximately 170/min to 110/min. Ventricular rhythms were first seen at about 120/min and fell to a minimum near 100/min over the next 30 minutes during which 3 more injections were given. Following the last injection, both sinus and ventricular rates recovered together over the next 1 to 2 hours. Ventricular rates recovered to between about 160 and 170/min, a rate just slightly lower than control sinus rates.

The ECG morphology for this sequence of rate changes is illustrated in FIG. 2 where a particular ECG configuration was chosen and followed it through the post drug recovery period. FIG. 2 shows the progression of ventricular slowing and recovery following four (4) intravenous injections of zatebradine (0.25 mg/kg each) as follows:

A: Baseline sinus rhythm (SR=165 beats/min) prior to the injection of UL-FS 49.

B: The conversion to ventricular rhythm a few minutes after the injections is illustrated for a ventricular rate (VR= 120 beats/min) near the peak slowing (VR minimum=110 beats/min).

C,D,E: The progressive return toward the faster ventricular rates, which presumably existed during control, is demonstrated for rates 139, 149, and 155 beats/min.

F: The conversion back to the baseline sinus rate is illustrated. The sinus rate (SR=155) is nearly back to the control (SR=165) and is comparable to the last ventricular rhythm measured.

EXAMPLE 5

Effect of atrial pacing during intravenous zatebradine

The slowing of the ectopic rhythm would favor dominance of sino-atrial rhythms were it not for the parallel slowing of the sinus node. However one could preserve the anti-arrhythmic character of the drug intervention by sustaining the pre-drug sino-atrial input with right atrial pacing. As previously shown in the Harris dog model, the anti-arrhythmic outcome following drug actions depends on the relative rates of the sinus and ectopic rhythms. In two additional 24 hour infarct preparations, the hypothesis that the drug effects were anti-arrhythmic in the presence of a constant atrial rate by applying multiple stimulus trains during the course of several hours before and after drug was tested.

During a control period we determined the threshold atrial pacing rate for capturing the ventricular pacemaker. We then studied this threshold rate for a prolonged period following intravenous injections of zatebradine. During the control period, we paced at rates starting with those slightly slower than the control sinus rate and increasing by intervals of 5 to 10 beats per minute. The threshold was the lowest rate of which 95–100% of the beats were captured during a one minute trial.

Results from one trial are depicted in FIG. 3. At a rate of 170/min (CL=0.353 msec), there were large numbers of ectopic beats (Panel A). As we slowly increased the rate, we determined the capture threshold to be 200/min (CL=333 msec). At this rate the ventricular activation pattern was solely determined by the paced atrial rate, as shown Panel B. Following IV zatebradine injection, there was 100% ectopic rhythm in the absence of pacing; yet, the ectopic rate could readily be captured at 160/min (CL=0.375) as shown in Panel C. Later during drug washout, the tissue could not be captured even at the higher rate of 100/min (CL=333 msec).

During the predrug control period, stimulus rates of 170/min (CL=350 msec) could not entrain the predominantly ventricular ectopic rhythm (panel A). The slowest rate achieving 95–100% capture for one minute was 200/min (CL=msec; panel B). Following i.v. drug application (0.25 mg/kg), there was 100% ectopic rhythm. This was entrained at 160/min (CL=390; panel C). Following drug washout, the minimum capture rate returned to high values, now in excess of 200/min (CL=300 msec; panel D). Bars under ECG traces indicate time when stimuli were delivered. The threshold rate was determined to be between the lowest rate where there was 100% capture during 1 min and the highest rate where there was 95% capture. (For some stimulus trains, there was a delay in achieving capture and an initial 15 seconds was allowed before declaring that the rate was below threshold.)

Figure 4:
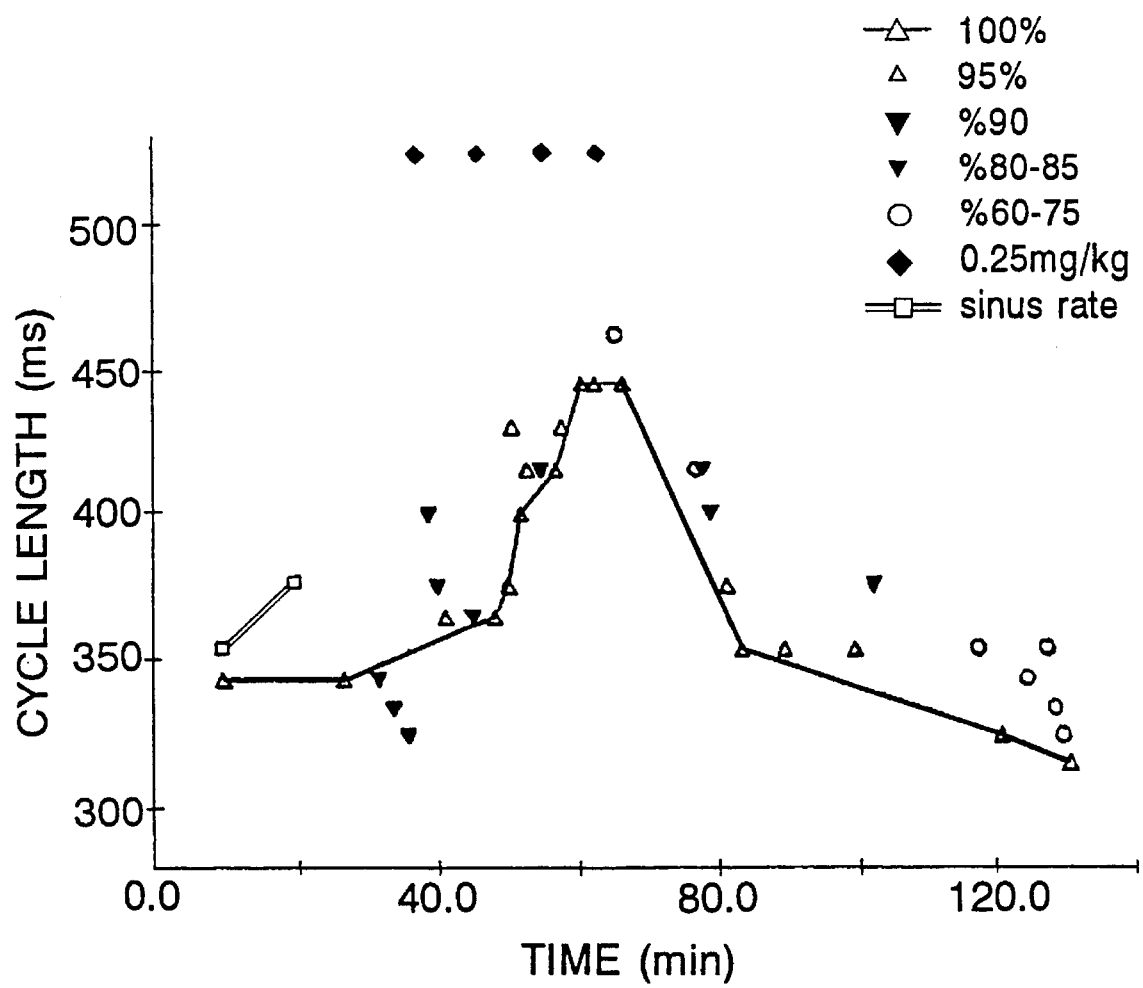
FIG. 4 depicts capture thresholds of the results of a series of 1 minute trains of stimuli applied to the right atria.

The results of a second trial are plotted as the change in capture threshold over time as shown if FIG. 4 and indicate that the CL for 95%–100% capture increased following intervention with the drug, but recovers with drug washout over a time course comparable to that of the recovery of ventricular rate (e.g. see FIG. 1A.). Therefore zatebradine shifts the threshold for capture to longer cycle lengths (28% mean increase; n=2).

The horizontal axis indicates experimental time. Cycle lengths in msec are indicated on the "y" axis for each train, while the plotting symbols indicate the percent of captured beats during one minute trains. Plotting symbols represent the following: 95–100% capture (triangles); 80–90% capture (inverted filled triangles); and 60–75% capture (circles). A line is drawn through all the triangles representing 100% capture. The open boxes are the initial sinus rates. The filled diamonds represent 0.25 mg/kg i.v. bolus injections of zatebradine. The largest CL value for 100% capture (343 msec; i.e. 175 beats/min) drops dramatically with i.v. injections (0.25 mg/kg, zatebradine) resulting in a maximum CL of 445 msec (135 beats/min). The threshold then slowly returns toward initial values over tens of minutes. Thus, after drug application, the percent ectopic activity increased dramatically; yet the heart could be captured at a CL which was increased by 28% over control.

Zatebradine has been shown to slow the ventricular rate, thereby allowing for capture of the ventricular ectopic rhythms using atrial pacing. This result has considerable therapeutic value since high rates place increased metabolic demand on the damaged heart and high rates coupled with ventricular arrhythmias compromise output. In an in-hospital setting where atrial pacing is already applied, zatebradine also may act as a successful therapeutic agent for slowing ventricular tachycardias. The ready availability and ease of employing pacing in the CCU makes this a readily testable therapeutic intervention both prophylactically and in treating ongoing ventricular tachycardias. Instances where atrial pacing already may have been initiated and which may be associated with delayed phase of myocardial infarction include, for example, (1) subsequent to heart block; and (2) postoperatively following cardiopulmonary bypass particularly where adrenergic stimulation is used. Additionally, zatebradine significantly lowers the rates needed for successful atrial pacing.

It has been shown that zatebradine slows the rate of ventricular ectopic rhythms. This slowing allows tier atrial pacing to capture the ventricles at a significantly lower rate (approximately 28%). Since zatebradine also slows the sinoatrial node, it must be used with atrial pacing to maintain sinus rates as ectopic rates are slowed. This restriction could be lifted under certain conditions, including, for example, (1) we could show that lower doses slowed ectopic rhythms more than sinus rhythms; (2) the drug was redesigned such that its use dependent properties now favored binding during the membrane potential trajectory of a depolarized subendocardial Purkinje fiber more than a sinus nodal fibers—this could be accomplished by altering the pKa of its charge(s); (3) we could show that in the presence of a second drug which was selective for Purkinje fibers over sinus node (e.g. a sodium channel blocker or a K-ATP channel activator), zatebradine would have a greater effect on the rate of the Purkinje fibers, already partially slowed. We have one observation in-vitro where a combination of calcium channel blocker and zatebradine stops the spontaneous rhythms.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A method of reducing the rate of a ventricular ectopic rhythm occurring in a subject during the delayed phase following a myocardial infarction which comprises administering an amount of zatebradine to the subject during the delayed phase effective to reduce the rate of the ventricular ectopic rhythm.

2. The method of claim 1, wherein administration comprises injecting zatebradine into the subject.

3. The method of claim 2, wherein the effective amount of zatebradine is from about 0.25 mg/kg to about 1.0 mg/kg of the body weight of the subject.

4. The method of claim 1, wherein the delayed phase is between about 18 to about 72 hours following the myocardial infarction.

5. The method of claim 1 wherein the reduction in the rate of the ventricular ectopic rhythm is by about 28%.

6. The method of claim 1, further comprising performing atrial pacing on the subject.

7. A method of capturing a ventricular ectopic rhythm in a subject during the delayed phase of following a myocardial infarction at a lower pacing rate which comprises
   i) administering an amount of zatebradine to the subject during the delayed phase effective to reduce the rate of the ventricular ectopic rhythm; and
   ii) performing atrial pacing on the subject during the delayed phase at a rate sufficient to capture the ventricular ectopic rhythm.

\* \* \* \* \*